(12) United States Patent
Sarma et al.

(10) Patent No.: US 6,902,901 B2
(45) Date of Patent: Jun. 7, 2005

(54) **POLYPEPTIDES USEFUL FOR DIAGNOSIS OF *ASPERGILLUS FUMIGATUS* AND A PROCESS OF PREPARING THE SAME**

(75) Inventors: Puranam U. Sarma, Dehli (IN); Taruna Madan, Dehli (IN); Priyanka Priyadarsiny, Dehli (IN); Seturan B. Katti, Lucknow (IN); Wahajul Haq, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/871,961

(22) Filed: Jun. 4, 2001

(65) Prior Publication Data

US 2002/0061544 A1 May 23, 2002

Related U.S. Application Data

(62) Division of application No. 09/184,938, filed on Nov. 3, 1998, now Pat. No. 6,262,231.

(30) Foreign Application Priority Data

| Mar. 24, 1998 | (IN) | 751/DEL/98 |
| Mar. 24, 1998 | (IN) | 752/DEL/98 |
| Mar. 24, 1998 | (IN) | 754/DEX/98 |
| Mar. 24, 1998 | (IN) | 746/DEL/98 |

(51) Int. Cl.$^7$ .................. G01N 33/53; A61K 38/00
(52) U.S. Cl. ............... 435/7.1; 435/7.2; 424/184.1; 530/300; 530/324
(58) Field of Search .................. 530/300, 324, 530/350, 25, 26; 424/184.1; 435/7.1, 7.2

(56) References Cited

U.S. PATENT DOCUMENTS 5,439,815 A   8/1995   Fitton et al.

OTHER PUBLICATIONS

Chauhan et al., J. Clin. Invest., vol. 97, No. 10 (May 1996) pp. 2324–2321.
Banerjee et al., J. Lab. Clin. Med., (Mar. 1996) pp. 153–262.
Arruda er al., J. Ex. Med., vol. 172 (Nov. 1990) pp. 1529–1532.
Kurup et al., Peptides, vol. 17, No. 2 (1996) pp. 183–190.
Teshima et al., Allergy Clin. Immunol., vol. 92, No. 5 (Nov. 1993) pp. 698–706.
Moser et al., J. Immuno., vol. 149, No. 2 (Jul. 1992).
Kumar et al., J. Allergy Clin. Immunol., vol. 91, No. 5 (May 1993) pp. 1024–1029.

*Primary Examiner*—Marjorie Moran
*Assistant Examiner*—Lori A. Clow
(74) *Attorney, Agent, or Firm*—Birch, Stewart, Kolasch & Birch, LLP

(57) ABSTRACT

The present invention relates to novel peptide sequences from the immunodominant region of an 18 kD major allergen/antigen of *Aspergillus fumigatus* from aa 6–22, comprising aa 10–20, aa 6–20, aa 14–20, aa 10–22, aa 6–13 and the peptide sequence resulting from the modification by substitution and/or by addition and/or deletion of one or more amino acid altering specified properties.

21 Claims, 11 Drawing Sheets

Figure 1

INQQLNPKTNKWEDKRY

Figure 2

LNPKTNKWEDK

Figure 3

INQQLNPK

Figure 4

INQQLNPKTNKWEDK

Figure 5

TNKWEDK

Figure 6

LNPKTNKWEDKRY

Fast Atom Bombardment Mass spectra for peptide (ID no.2)

Fast Atom Bombardment Mass spectra for peptide (ID no.3)

Fast Atom Bombardment Mass spectra for peptide (ID no.4)

Fast Atom Bombardment Mass spectra for peptide (ID no.5)

Fast Atom Bombardment Mass spectra for peptide (ID no.6)

High performance liquid chromatography profile for peptide (ID no.2)

High performance liquid chromatography profile for peptide (ID no.3)

High performance liquid chromatography profile for peptide (ID no.4)

High performance liquid chromatography profile for peptide (ID no.5)

High performance liquid chromatography profile for peptide (ID no.6)

POLYPEPTIDES USEFUL FOR DIAGNOSIS OF *ASPERGILLUS FUMIGATUS* AND A PROCESS OF PREPARING THE SAME

This application is a divisional of application Ser. No. 09/184,938, filed on Nov. 3, 1998, now U.S. Pat. No. 6,262,231 the entire contents of which are hereby incorporated by reference and for which priority is claimed under 35 U.S.C. § 120; and this application claims priority of application Ser. No. 746/DEL/98; 751/DEL/98; 752/DEL/98; and 754/DEL/98 filed in INDIA on Mar. 24, 1998 under 35 U.S.C. §119.

FIELD OF INVENTION

The present invention relates to novel peptides of *Aspergillus fumigatus* having an amino acid sequence selected from the immunodominant region delimited by aa 6–22 of the 18 kD allergen/antigen useful for immunodiagnosis.

The invention further relates to a method for using any of the peptide sequences of the present invention for the diagnosis of *aspergillosis*.

The invention also relates to a method for using the peptide sequence from aa 10–20 of the present invention for the diagnosis of *aspergillosis*.

The invention also relates to DNA sequences encoding for the peptides of the present invention.

The invention further relates to the DNA and RNA probes constructed on the basis of the peptide sequences of the present invention.

The invention also relates to recombinantly expressed peptides comprising the sequences of the peptides of the present invention.

The invention also relates to an immunodiagnostic kit using the peptides of the present invention for diagnosis of *aspergillosis*.

The invention further relates to a DNA based diagnostic kit using the DNA, cDNA or RNA sequences based on the sequences of the peptides of the present invention.

A field of use is the use of the said synthetic peptides for the preparation of a vaccine against *aspergillosis*.

A further field of use is the use of the said synthetic peptides for the detection of T-cell proliferation by in vitro tests.

A further field of use is use of said synthetic peptides for intradermal skin testing of *aspergillosis*.

BACKGROUND OF THE INVENTION

The fungus, *Aspergillus fumigatus* causes a wide spectrum of human arid animal disorders such as allergic bronchopulmonary *aspergillosis* (ABPA), extrinsic allergic alveolitis, *aspergilloma* and invasive *aspergillosis*. An invasive form of *aspergillosis* is becoming increasingly important in immunosuppressed conditions due to environmental pollution, enhanced use of chemotherapeutic drugs and antibiotics etc. The most susceptible hosts are immunocompromised patients, such as cases with organ transplant, leukemia or acquired immunodeficiency syndrome (AIDS).

Currently available tests for identification of this fungus is based on tedious, time consuming, less sensitive methods such as microscopy, cultures, electrophoresis and immunodiffusion. Many clinical features of *aspergillosis* are similar to tuberculosis and most of the *aspergillosis* patients are put on antituberculous therapy. The microscopy of the specimen for identification of *Aspergillus* hyphae is not easy under field conditions and specimens from the patients in the early stages of disease are often negative in the direct mounts. Further, the fungal culture generally takes 3–4 weeks and is expensive as a routine diagnostic measure. The widely used skin testing for *Aspergillus* allergic patients lacks sensitivity and specificity as the mixture of allergens used for testing is not well characterised and needs standardisation. The steroid therapy used for allergic patients and chemotherapy for invasive patients are more beneficial when employed in the early stages of the disease. Consequent to these factors, many investigators recommend that early diagnosis of aspergillosis should be considered as a priority area of research and development.

Peptides mimicking the epitopes in native antigens have been utilised in diagnosis as well as therapy of hepatitis, influenza, malaria, AIDS etc. Peptides based diagnosis of *aspergillosis* would be standardised and cost effective. Thus, the focus of research in *aspergillosis* pertaining to these aspects lies in the identification and purification of diagnostically relevant allergens and antigens of *A. fumigatus* and identification and synthesis of the epitopic peptides with sequences derived from the diagnostically relevant allergens and antigens.

PRIOR ART REFERENCES

Many investigators have identified protein allergens and antigens of *A. fumigatus* which have potential immunodiagnostic application. The N-terminal and internal amino acid sequences of many of these allergens/antigens have been published. The N-terminal amino acid sequences of some of these are presented in Table 1.

TABLE 1

*A. fumigatus* protein allergens/antigens identified by N-terminal amino acid sequences.

| Investigators | Antigens and N-terminus | |
|---|---|---|
| Teshima et al, 1993 | 55 kDa: ATPHEPVFFSWDAGAVTSFP | (SEQ ID NO:8) |
| Kumar et al, 1993 | 65 kDa: AQNRQTLAKLLRYQSTKSG | (SEQ ID NO:9) |
| Moser et al, 1992 | 18 kDa: ATWTCINQQLNPKTNKWE | (SEQ ID NO:10) |
| Arruda et al, 1992 | 18 kDa: ATWTCINQQLNPKTNKWE | (SEQ ID NO:10) |
| Banerjee et al, 1996 | 34 kDa: SARDEAGLNEAVELARHAK | (SEQ ID NO:11) |

However, none of the above allergens/antigens have been introduced as immunodiagnostic test products.

An alternative method of diagnosis of *aspergillosis* has been the use of polymerase chain reaction (PCR) and hybridisation. Various groups have identified and synthesized primers for genes specific to *A. fumigatus*. Our group also has developed a PCR based colorimetric diagnostic test specific for *A. fumigatus*. Gene based tests are highly sensitive and specific in comparison to immunodiagnosis. However, at present no gene based diagnostic kit for *aspergillosis* is available in the market as routine use of this test proves very expensive.

At present, an immunodiagnostic ELISA kit based on mixture of potent antigens has been formulated by the applicants. The present test is antibody based and thus is not useful for invasive patients.

The peptide based immunodiagnostic reagents are cost effective, homogeneous and more specific. Antigenic determinants of Asp fl have been synthesised by Kurup et al, 1995 but the diagnostic relevance of these peptides have not been indicated. As such, no peptide based immunodiagnostic kit is available in the market at present.

SUMMARY OF THE INVENTION

The present invention relates to novel peptide sequences from the immunodominant region of an 18 kD major allergen/antigen of *Aspergillus fumigatus* from aa 6–22, comprising aa 10–20, aa 6–20, aa 14–20, aa 10–22, aa 6–13 and the peptide sequence resulting from the modification by substitution and/or by addition and/or deletion of one or more amino acid altering specified properties. The peptides are useful in enzyme linked immunosorbent assay (ELISA) for the diagnosis of aspergillosis. They have lymphoproliferative as well as immunogenic properties and hence are potentially applicable in immunotherapy and immunoprophylaxis of aspergillosis. They are also able to stimulate the histamine release from sensitised mast cells of patients.

DETAILED DESCRIPTION

The present invention relates to epitopic peptides of an 18 kD major allergen/antigen of *Aspergillus fumigatus* (strain 285, isolated from the sputum of an ABPA patient similar to the ATCC strain AF-102; ATCC-42202). *A. fumigatus* causes allergic as well as invasive *aspergillosis* worldwide. Five epitopes were identified on the 18 kD major allergen/antigen in the immunodominant region from aa 6–22, comprising aa 10–20, aa 6–20, aa 14–20, aa 10–22, aa 6–13 and these epitopic sequences were synthesised by solid phase method. The peptides were able to bind *A. fumigatus* specific antibodies in the sera of patients and hence, useful in enzyme linked immunosorbent assay (ELISA) for the diagnosis of *aspergillosis*. They have lymphoproliferative as well as immunogenic properties and hence are potentially applicable in immunotherapy and immunoprophylaxis of *aspergillosis*. They were also able to stimulate the histamine release from sensitised mast cells of patients.

The said peptides of the present invention are able to bind the *A. fumigatus* specific IgG and IgE antibodies in the sera of patients of *aspergillosis*. Further, they are able to raise significant amount of antibodies in the mice and these polyclonal antibodies can be used for diagnosis of invasive *aspergillosis*. These novel synthetic peptides are also able to stimulate histamine release from the sensitised mast cells of allergic bronchopulmonary *aspergillosis* patients and hence can replace crude mixture of allergens for skin testing.

The applicants have developed an enzyme linked immunosorbent assay (ELISA) based sensitive test using a mixture of potent *Aspergillus fumigatus* antigens which provides a rapid diagnosis in early stages of the disease. However, there are variations in the mixture obtained from various clinical isolates of *Aspergillus fumigatus*.

The present invention relates to (i) peptides, from the immunodominant region aa 6–22, comprising to aa 10–20, aa 6–20, aa 14–20, aa 10–22, aa 6–13 and the peptide sequences resulting from the modification by substitution and/or by addition and/or deletion of one or more amino acid altering specified properties; (ii) recombinantly expressed peptides comprising of at least one of the sequences as in (i); (iii) DNA/RNA probes hybridising with DNA sequences encoding for the peptides said in (i); (iv) monoclonal or polyclonal antibodies raised against a peptide as in (i); (v) an immunodiagnostic kit for *aspergillosis* based on peptides as in (I) and (vi) a gene based diagnostic kit for *aspergillosis* based on nucleotide probes as in (III).

Accordingly, the present invention provides *Aspergillus fumigatus* peptides having an aminoacid, sequence selected from the immunodominant region delimited by aa 6–22 of 18 kD allergen/antigen, the said peptides having following sequences useful for immunodiagnosis of *aspergillosis*;

Isoleucinyl-asparaginyl-glutamyl-glutamyl-leucyl-asparaginyl-prolyl-lysyl-threonyl-asparaginyl-lysyl-tryptophanyl-glutamyl-aspartyl-lysyl [INQQLNPKT-NKWEDKRY] (aa 6–22) (SEQ ID NO:1)

Leucyl-asparginyl-prolyl-lysyl-threonyl-asparginyl-lysyl-tryptophanyl-glutamyl-aspartyl-lysyl-arginyl-tyrosine [LNPKTNKWEDK] (aa 10–20) (SEQ ID NO:2)

Isoleucyl-asparginyl-gluamyl-glutamyl-leucyl-asparginyl-prolyl-lysyl [INQQLNPK] (aa 6–14) (SEQ ID NO:3)

Isoleucinyl-asparginyl-glutamyl-glutamyl-leucyl-asparginyl-prolyl-lysyl-threonyl-asparginyl-lysyl-tryptophanyl-glutamyl-aspartyl-lysyl INQQLNPKT-NKWEDK (aa 6–20) (SEQ ID NO: 4)

Threonyl-asparginyl-lysyl-tryptophanyl-glutamyl-aspartyl-lysine [TNKWEDK] (aa 14–20) (SEQ ID NO: 5)

Lysyl-lysyl-leucyl-asparginyl-prolyl-lysyl-threonyl-asparginyl-lysyl-tryptophanyl-glutamyl-aspartyl-lysyl-lysyl-lysine (aa 10–22) [LNPKTNKWEDKRY] (SEQ ID NO: 6)

The said peptides were synthesised using solid phase peptide synthesis method comprising the following features:

1. Suitably protecting the first amino acid of the C-terminal of the said peptide which is attached with appropriately functionalised polystyrene resin (such as Merrifield, PAM or Wang resin) in presence of organic solvents (for eg. Methylene chloride, dimethylformamide, ether, petroleum ether, acetic acid, methanol etc.)

2. The alpha-amino side chain of the amino acid should be protected to begin with using BOC/FMOC/Z/CI-Z chemistry.

3. The protecting moiety from the alpha-amino group of the amino acid is removed later by hydrochloride acid/dioxane, trifluoroacetric acid, piperidine etc.

4. The next suitably protected amino acid in the sequence of the peptide is coupled with the already resin coupled amino acid using coupling reagents such as DCC, BOP reagent, HBTU etc.

5. The steps of coupling and deblocking are repeated with other suitable protected amino acids of the peptide sequence.

6. After the completion of coupling of all the required amino acids of the peptide sequence, the peptide is cleaved from the resin by acid treatment followed by neutralisation and deblocking the protecting groups.

7. The cleaved peptide is subsequently subjected to hydrogenation and repeated precipitation.

In a preferred embodiment, the invention envisages repeating the steps of coupling and deblocking with suitably protected group (a) lysine, leucine, proline, lysine, threonine, asparagine, lysine, tryptophan, glutamine, aspartic acid, lysine, lysine, lysine, (b) lysine, tryptophan, glutamine, aspartic acid, lysine (c) glutamine, glutamine, leucine, proline, lysine, (d) proline, lysine, threonine, asparagine, lysine, tryptophan, glutamic acid, aspartic acid, lysine, arginine, tyrosine, or (e) glutamine, glutamine, leucine, asparagine, proline, lysine, threonine, asparagine, lysine, tryptophan, glutamic acid, aspartic acid, lysine amino acids, to obtain peptides with the following sequences respectively:

(a) Lysyl-lysyl-leucyl-asparginyl-prolyl-lysyl-threonyl-asparginyl-lysyl-tryptophanyl-glutamyl-aspartyl-lysyl-lysyl-lysine (KKLNPKTNKWEDKKK) (SED ID NO: 7), (b) Threonyl-asparginyl-lysyl-tryptophanyl-glutamyl-asparty-lysine, (TNKWEDK) (SEQ ID NO: 5), (c) Isoleucyl-asparaginyl-glutaminyl-glutaminyl-leucyl-asparginyl-proly-lysine (INQQLNPK) (SEQ ID NO: 3), (d) Leucyl-asparginyl-prolyl-lysyl-threonyl-asparginyl-lysyl-tryptophanyl-glutamyl-aspartyl-lysyl-arginyl-tyrosine (LNPKTNKWEDKRY) (SEQ ID NO: 6), or (e) Isoleucinyl-asparaginyl-glutaminyl-glutaminyl-leucyl-asparaginyl-prolyl-lysyl-threonyl-asparaginyl-lysyl-tryptophanyl-glutamyl-aspartyl-lysyl (INQQLN-PKTNKWEDK) (SEQ ID NO: 4).

In another embodiment of the invention the polystyrene resin used is such as Merrifield resin, PAM resin, Wang resin etc., and the attachment of suitably protected isoleucine with the resin may be carried out using ester or amide linkage with DCC/DMAP, cesium salt or using a linker (for PAM resin) by DCC alone.

In another embodiment the organic solvents used may be such as methylene chloride, dicholoromethane, dimethylformamide, ether, petroleum ether, acetic acid, methanol N-methyl-2-pyrolidone etc.

In yet another embodiment of the invention deblocking agents used may be such as HCl/dioxane, TFA/CH$_2$Cl$_2$ HBr/AcOH, formic acid etc.

In another embodiment of the invention coupling may be carried our by using agents such as dicyclohexylcarbodiimide, mixed anhydride, active esters, BOP reagent, BHTU, triethylamine and ethylchloroformate.

In another embodiment of the invention cleavage of the peptide from the resin may be carried out using the acids such as HBr/AcOH, TFA/TFMSA, liquid ammonia, liquid HF and trifluoroacetic acid etc.

In another embodiment of the invention the neutralisation may be carried out by tertiary bases such as N-methylmorpholine triethyl amine or diisopropylethyl amine.

In another embodiment of the invention hydrogenation agents used may be such as Pd/C, Palladium chloride, Rhodium/C, adams catalysts and palladium black etc.

The present invention further relates to a method for using any of the peptide sequences stated above and falling under the immunodominant region delimited by aa 6–22 for the diagnosis of *aspergillosis* which comprises;

a. collecting body fluid sample from a patient and separating the fluid from the cells, b. incubating the said peptides with the fluid obtained in the step a, c. separating the residual unbound antibodies from the resultant incubation mixture in step b, d. incubating the antibodies obtained in step c with the mixture of allergens/antigens of *A. fumigatus* coated on the polystyrene ELISA plates, e. washing the excess antibodies from the ELISA plates with an appropriate buffer, f. incubating the washed plates from step e with anti-human IgG/IgE conjugated with an appropriate enzyme, g. washing the excess conjugate from the ELISA plates with an appropriate buffer, h. adding an appropriate soluble substrate for the enzyme used in step f, and i. reading the absorbance values of the wells of ELISA plates in an ELISA reader at an appropriate wavelength, wherein the acuteness of the disease is inversely related to the absorbance value.

Furthermore, the present invention relates to a method for using the peptide sequence as stated above and from aa 10–20 for the diagnosis of *aspergillosis* which further comprises;

a. collecting body fluid sample from a patient and separating the fluid from the cells, b. incubating the patient fluid obtained in step a with the said peptide coated on the polystyrene ELISA plates, c. washing the excess antibodies from the ELISA plates with an appropriate buffer, d. incubating the washed plates from step c with anti-human IgG/IgE conjugated with an appropriate enzyme, e. washing the excess conjugate from the ELISA plates with an appropriate buffer, f. adding an appropriate soluble substrate for the enzyme used in step d, and g. reading the absorbance values of the wells of ELISA plates in an ELISA reader at an appropriate wavelength, wherein the acuteness of the disease is directly related to the absorbance value.

In an embodiment of the invention, the body fluid used may be selected from blood, serum, cerebrospinal fluid, pleural fluids and saliva.

In another embodiment of the invention, *A. fumigatus* allergens/antigens used are either obtained commercially or prepared by known methods.

In another embodiment of the invention, the buffer used is selected from Phosphate buffered saline or Tris buffered saline.

In an embodiment of the invention, the epitopic sequences are characterised by Fast Atom Bombarding mass spectroscopy (FABMS) & High Pressure Liquid Chromatography (HPLC) as shown in FIGS. 7–16.

In a further embodiment of the invention, the conjugate used is selected from anti-human IgG/IgE peroxidase or anti-human IgG/IgE alkaline phosphatase.

In an embodiment of the invention, body fluid used may be selected from blood, serum, cerebrospinal fluid, pleural fluids and saliva.

In another embodiment of the invention, the *A. fumigatus* allergens/antigens used are either obtained commercially or prepared by known methods.

In another embodiment of the invention, the buffer used is selected from Phosphate buffered saline or Tris buffered saline.

In a further embodiment of the invention, the conjugate used is selected from anti-human IgG/IgE peroxidase or anti-human IgG/IgE alkaline phosphatase.

In another embodiment of the invention, the substrate used is o-phenyldiamine or nitroblue tetrazolium (NBT).

In another embodiment of the invention, *Aspergillus fumigatus* strains used is ATCC strain AF-102; ATCC-42202.

In another embodiment of the invention, antibody binding regions termed epitopes are identified through computer programmes.

In another embodiment of the invention, claimed peptides are synthesised by solid phase synthesis.

In a feature of the present invention, claimed peptides are also useful for lymphoproliferation of lymphocytes isolated from the patients.

In another feature of the invention, claimed peptides are useful to raise antibodies against the said peptides in animals.

In another feature of the present invention, claimed peptides are also useful for immunotherapy and protection against *Aspergillus fumigatus*.

The claimed invention also relates to DNA sequences encoding the claimed peptides.

The claimed invention also relates to a DNA or RNA probe constructed on the basis of sequences of the claimed peptides.

The claimed invention also relates to recombinant peptides comprising of at least one of the sequences of the claimed peptides.

The claimed invention also relates to an immunodiagnostic kit using the claimed peptides according to the methods described for diagnosis of *aspergillosis*.

The claimed invention also relates to a DNA based diagnostic kit using the DNA, cDNA or RNA sequences constructed based on the sequences of the claimed peptides.

The present invention is exemplified by but not limited to the diagnosis, therapy or prophylaxis of diseases, especially diagnosis of *A. fumigatus* infection. Epidemiological screening, forensic investigations, determination of food contaminations, public health surveys, preventive medicine, veterinary and agricultural applications with regard to the diagnosis of infectious agents may be covered by this disclosure.

BRIEF DESCRIPTION OF THE DRAWINGS

FIG. 1 shows the sequence of isoleucinyl-asparaginyl-glutamyl-glutamyl-leucyl-asparaginyl-prolyl-lysyl-threonyl-asparaginyl-lysyl-tryptophanyl-glutamyl-aspartyl-lysyl [INQQLNPKTNKWEDKRY] (-aa 6–22) [SEQ ID NO: 1].

FIG. 2 shows the polypeptide sequence of Leucyl-asparginyl-prolyl-lysyl-threonyl-asparginyl-lysyl-tryptophanyl-glutamyl-aspartyl-lysyl-arginyl-tyrosine [LNPKTNKWEDK] (aa 10–20) [SEQ ID NO: 2].

FIG. 3 provides the sequence of Isoleucyl-asparginyl-gluamyl-glutamyl-leucyl-asparginyl-prolyl-lysyl [INQQLNPK] (aa 6–14) [SEQ ID NO: 3].

FIG. 4 provides the sequence of soleucinyl-asparginyl-glutamyl-glutamyl-leucyl-asparginyl-prolyl-lysyl-threonyl-asparginyl-lysyl-tryptophanyl-glutamyl-aspartyl-lysyl INQQLNPKTNKWEDK (aa 6–20) [SEQ ID NO:4].

FIG. 5 provides the sequence of Threonyl-asparginyl-lysyl-tryptophanyl-glutamyl-aspartyl-lysine [TNKWEDK] (aa 14–20) [SEQ ID NO:5].

FIG. 6 provides the sequence of Lysyl-lysyl-leucyl-asparginyl-prolyl-lysyl-threonyl-asparginyl-lysyl-tryptophanyl-glutamyl-aspartyl-lysyl-lysyl-lysine [LNPKTNKWEDKRY] (aa 10–22) [SEQ ID NO:6].

EXAMPLE 1

Identification of Peptide Epitopes in the 18 kD of *A. fumigatus*

Figure 7:
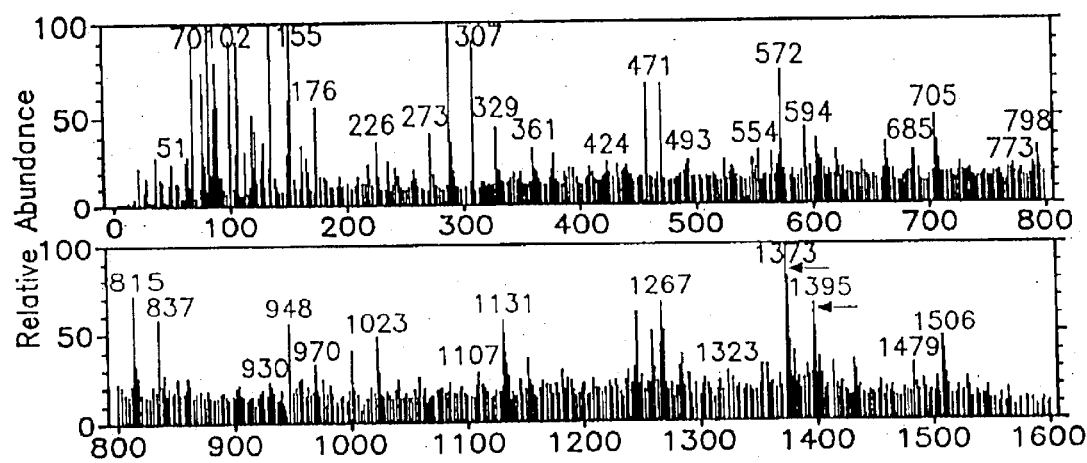
FIG. 7 of the accompanying drawings shows Fast Atom Bombardment Mass spectra for peptide (SEQ ID NO: 2).
Figure 8:
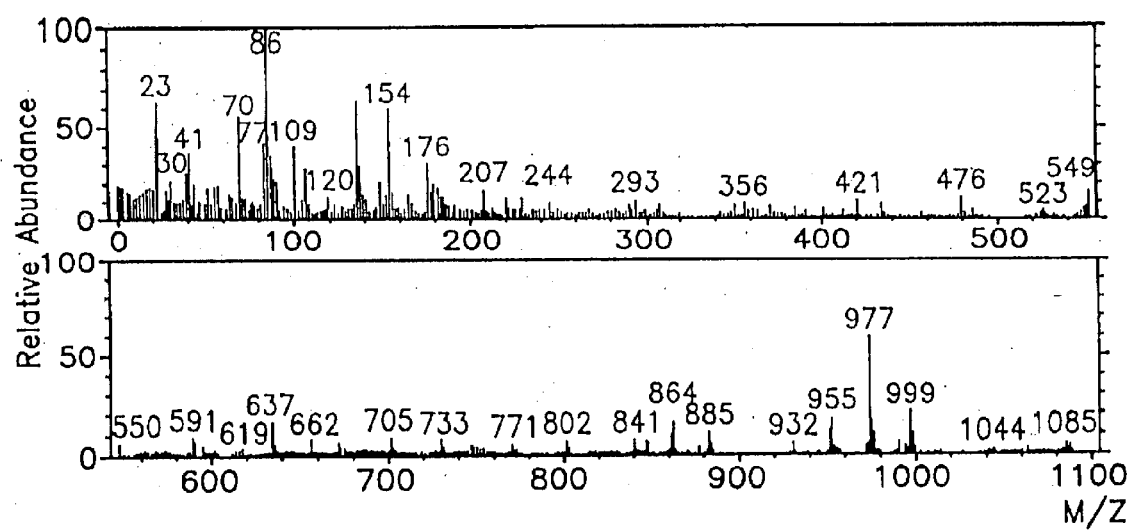
FIG. 8 of the accompanying drawings shows Fast Atom Bombardment Mass spectra for peptide (SEQ ID NO: 3).
Figure 9:
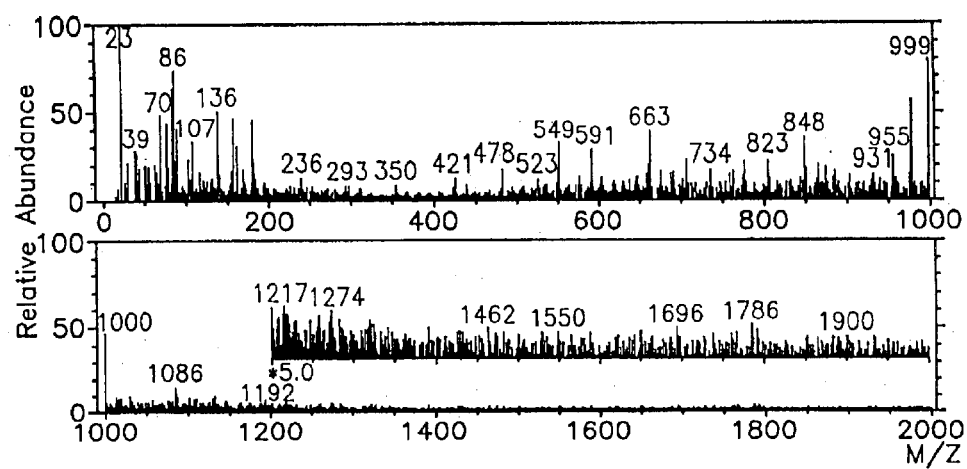
FIG. 9 of the accompanying drawings shows Fast Atom Bombardment Mass spectra for peptide (SEQ ID NO: 4).
Figure 10:
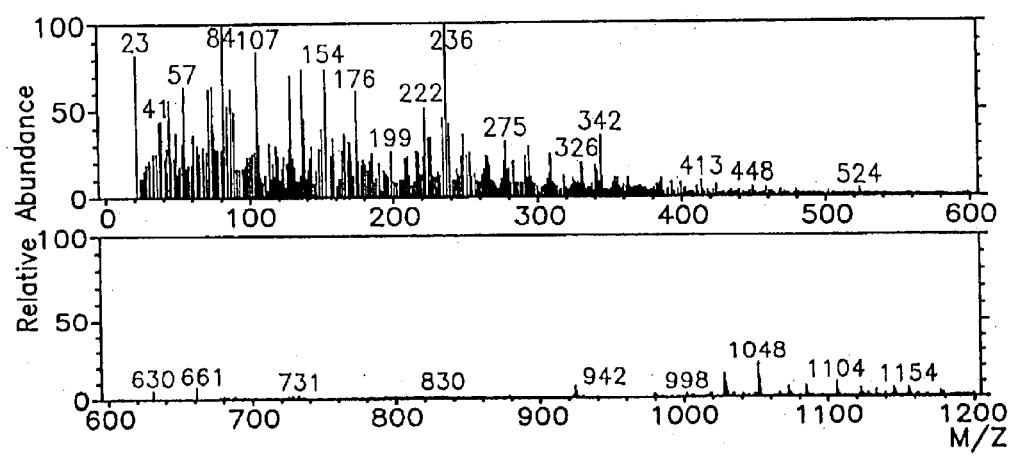
FIG. 10 of the accompanying drawings shows Fast Atom Bombardment Mass spectra for peptide (SEQ ID NO: 5).
Figure 11:
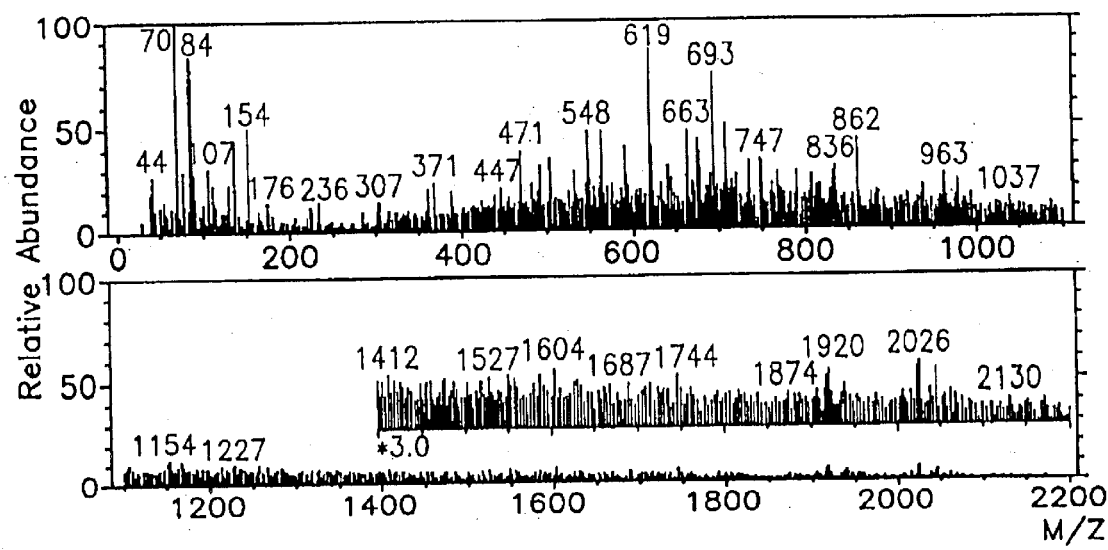
FIG. 11 of the accompanying drawings shows Fast Atom Bombardment Mass spectra for peptide (SEQ ID NO:6).
Figure 12:
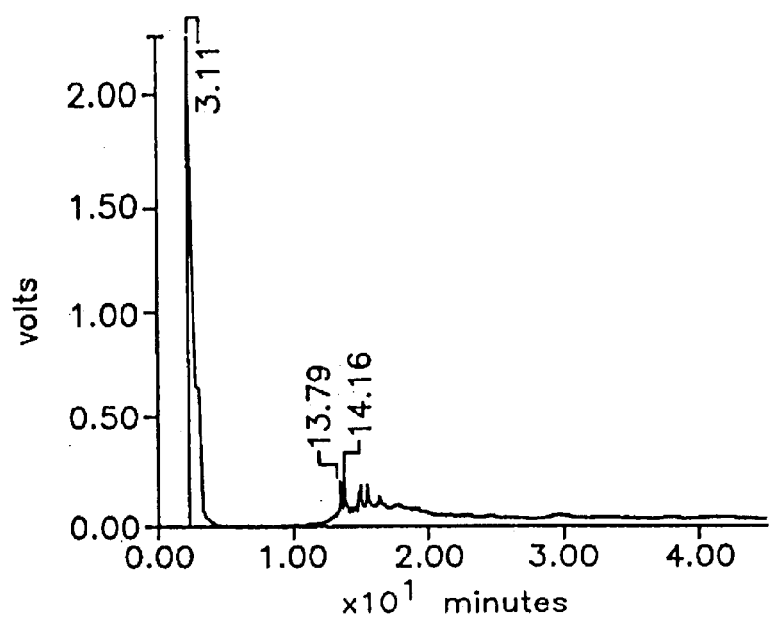
FIG. 12 of the accompanying drawings shows High performance liquid chromatography profile for peptide (SEQ ID NO:2).
Figure 13:
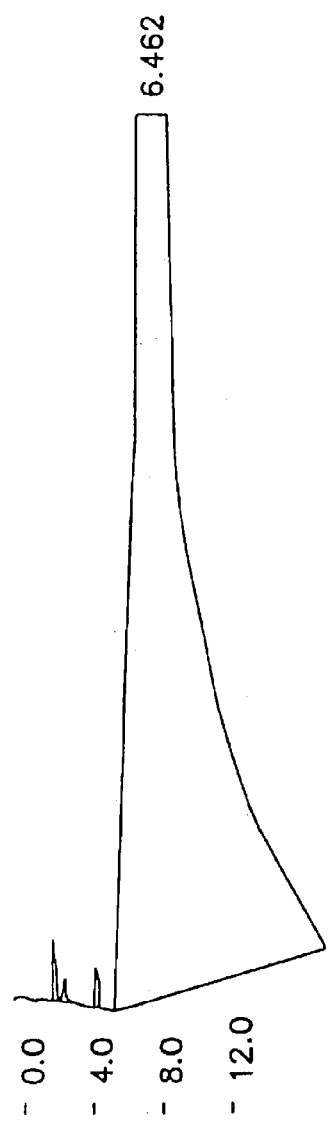
FIG. 13 of the accompanying drawings shows High performance liquid chromatography profile for peptide (SEQ ID NO:3).
Figure 14:
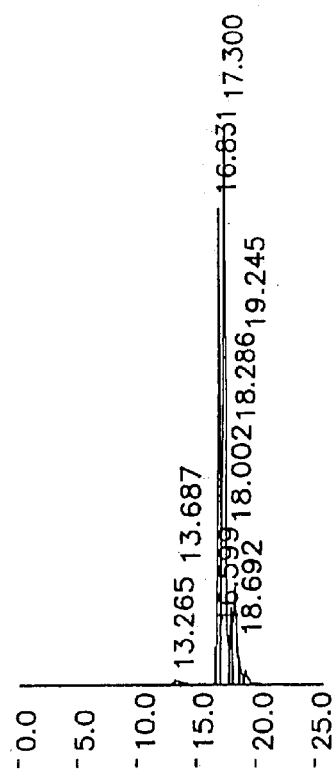
FIG. 14 of the accompanying drawings shows High performance liquid chromatography profile for peptide (SEQ ID NO:4).
Figure 15:
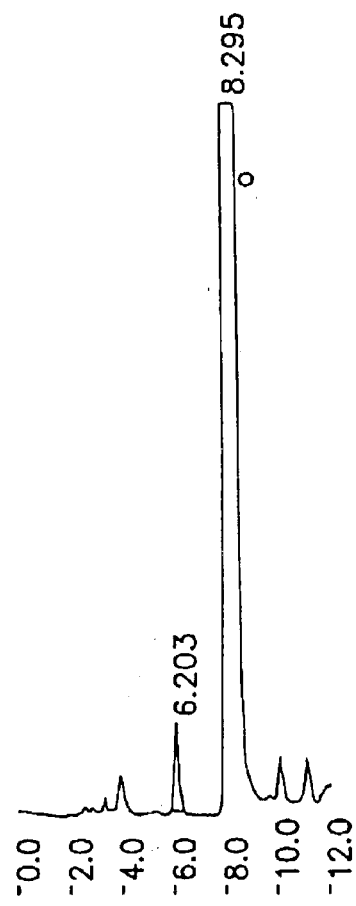
FIG. 15 of the accompanying drawings shows High performance liquid chromatography profile for peptide (SEQ ID NO:5).
Figure 16:
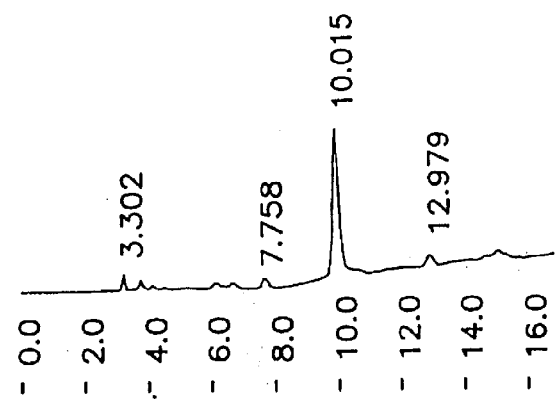
FIG. 16 of the accompanying drawings shows High performance liquid chromatography profile for peptide (SEQ ID NO:6).

An allergen/antigen with an apparent molecular weight of 18 kD was isolated, purified and characterised from the third week culture filtrate of *Aspergillus fumigatus* (strain 285, isolated from the sputum of an ABPA patient similar to the ATCC strain AF-102; ATCC-42202). This antigen is cytotoxic to mammalian cell lines and possesses ribonuclease activity. Homogenity of the purified 18 kD antigen was established on Sodium dodecyl sulfate-polyacrylamide electrophoresis (SDS-PAGE) and high pressure liquid chromatography (HPLC) Monoclonal antibodies raised against 18 kD allergen/antigen (Asp fl) (Moser et al, 1992 and Arruda et al, 1992) of an American type culture collection (ATCC) strain of *A. fumigatus* (AF-102; ATCC-42202) reacted with the 18 kD allergen/antigen of the present invention isolated from the *A. fumigatus* strain 285. The gene for 18 kD allergen/antigen was identified, sequenced and overexpressed. The deduced aminoacid sequence of the 18 kD allergen/antigen was analysed by ten different algorithmic programmes based on hydrophilicity, amphipathy, accessibility, mobility, antigenicity etc. This computerised analysis revealed presence of few sequences of T & B cell epitopic nature. Five of these probable epitopes were synthesised by solid phase method and studied in detail. Synthesised epitopic sequences were characterised by Fast atom bombarding mass spectroscopy (FABMS) and High pressure liquid chromatography (HPLC) (FIGS. 7 to 16).

EXAMPLE 2

Immunoreactivity of Synthetic Peptides

Demonstration that synthetic peptides react with sera of *aspergillosis* patients. Sera derived from 25 healthy persons and 30 culture proven allergic bronchopulmonary *aspergillosis* patients were probed with synthetic peptides of the present invention for *A. fumigatus* specific antibodies. NUNC ELISA plates were coated with 0–1 ug/ml of peptide in carbonate-bicarbonate buffer, 0.01 M, pH 9.6 for 2 h at 37° C. The unreacted sites were blocked with bovine serum albumin in phosphate buffered saline, 0.01 M, pH 7.4. Diluted sera (1:100) of patients or healthy controls was added to the wells and Incubated for 3 h at 37° C. Washed plates received anti-human IgG-HRP conjugate for 1.5 h at 37° C. washed plates were then assayed with o-phenylene diamine substrate and read at 492 nm. The results are shown in Table-2.

EXAMPLE-3

Demonstration that Synthetic Peptides Elicit Antibodies among Experimental Animals Each synthetic peptide (300 ug/150 ul saline) was emulsified with an equal volume of Freund's incomplete adjuvant and used for intraperitoneal immunisation of 3 BALB/c mice. IgG antibodies in the serum collected from these mice 30 days after immunization bound with mixture of *A. fumigatus* allergens/antigens and purified 18 kD allergen/antigen in ELISA. The results are shown in Table-3.

Thus, this experiment confirms that a polyclonal or monoclonal antibody can be procured in the mouse which recognise the allergens/antigens of *A. fumigatus* or substructures (peptides) thereof. Such antibodies, in particular the monoclonal antibodies, can be used in antigen detection method like the sandwich ELISA for the detection of the *A. fumigatus* antigens in the human invasive *aspergillosis* specimens leading to immunodiagnosis of *aspergillosis*.

EXAMPLE-4
Demonstration that Synthetic Peptides are Lymphoproliferative

Peripheral blood lymphocytes (PBL) from healthy donors and *aspergillosis* patients were fractionated and $2\times10^6$ cells/well were cultured in presence or absence of synthetic peptides for 6 days in RPMI 1640 medium with 10% autologous serum. The supernatant medium was collected for cytokine analysis and 0.5 mg/ml solution of MTT was added to each well for 30 min. before harvesting cultures with acidified isopropanol. Absorbance was measured at 590 nm. The results showed that all the five peptides were more lymphoproliferative to the lymphocytes of the *aspergillosis* patients (five patients only) in comparison to the lymphocytes of healthy controls.

Thus this experiment indicates that the synthetic peptides of the present invention can be used to stimulate human peripheral blood lymphocytes. Since, stimulated lymphocytes elaborate several cellular growth and differentiation factors which contribute to the vaccine effect of synthetic peptides, they can be used at the first instance as a vaccine against *aspergillosis* and also for nonspecifically boosting cellular immunity. The results are shown in Table-4.

EXAMPLE-5
Demonstration that Synthetic Peptides Stimulate Release of Histamine from Sensitised Mast Cells of Patients Whole blood (heparinised) was incubated with the peptides for 30 min at 37° C. in polystyrene plates followed by centrifugation and collection of supernatants. The supernatants were acylated and were assayed for acylated histamine by histamine assay kit (Immunotech International). The results are shown in Table-5. Their ability to stimulate histamine release in vitro indicates that these peptides may be potential reagents for skin testing.

Discussion and Summary of Test Results

The present invention describes the immunochemical properties of five novel synthetic peptides with sequences derived from 18 kDa allergen/antigen of *A. fumigatus*. *A. fumigatus* causes allergic *aspergillosis* in atopic population and invasive *aspergillosis* in immunocompromised patients worldwide. Because of inadequacy of the diagnostic procedures presently available, the disease is not diagnosed at the early stages. The focus of research in recent years has been the development of immunodiagnostic methods for detecting *aspergillosis* at an early stage as well as identification of suitable candidates which can provide protection against the disease.

The studies described in this Invention show that five novel peptides with sequences derived from 18 kD allergen/antigen of *A. fumigatus* have imunodiagnostic potential. The T-cell stimulating property of the peptides indicates that they could be used in therapy and vaccination for *aspergillosis*.

The main advantages of the synthetic peptides of the present invention for possible application in diagnosis and therapy are:

1. Synthetic epitopic peptides with required immunological activity would facilitate use of pure, homogeneous, cost effective, specific diagnostic reagent. Such a reagent is anticipated to find a place in International market of Diagnostics for universal application.

2. Simple and rapid diagnostic technologies can easily be developed with such reagents.

3. Identified antigenic determinants may easily replace crude antigens of current use for intradermal skin testing.

4. The whole protein antigens need not be used for serodiagnosis. Small synthetic peptide epitopes facilitate fidelity thereby enhance reproducibility. Current peptides can replace the native antigen of *A. fumigatus* for diagnosis.

5. An immunodiagnostic kit based on the polyclonal or monoclonal antibodies raised against these antigenic determinants could also be used for detection of antigen in immunocompromised hosts.

6. The peptides induce cellular immune responses relevant to protective immunity, and may also find use in desensitisation.

TABLE 2

ELISA absorbance values for Specific IgG/IgE binding of the peptides claimed

| | Absorbance at 490 nm | | | |
|---|---|---|---|---|
| | Patient sera | | Normal sera | |
| Peptides | Specific IgG | Specific IgE | Specific IgG | Specific IgE |
| pep 2 | 0.852 | 0.473 | 0.09 | 0.039 |
| pep 3 | 0.674 | 0.256 | 0.011 | 0.042 |
| pep 4 | 0.845 | 0.235 | 0.006 | 0.028 |
| pep 5 | 0.850 | 0.208 | 0.012 | 0.032 |
| pep 6 | 0.828 | 0.145 | 0.004 | 0.033 |
| three week culture filterate | 0.956 | 0.468 | 0.030 | 0.062 |
| HIV peptide | 0.078 | 0.058 | 0.051 | 0.037 |

TABLE 3

ELISA absorbance values for specific IgG antibodies in mice raised against the peptides claimed

| | Absorbance at 490 nm | |
|---|---|---|
| Peptides | Immunised mice | Control mice |
| pep 2 | 0.636 | 0.056 |
| pep 3 | 0.434 | 0.062 |
| pep 4 | 0.526 | 0.048 |
| pep 5 | 0.498 | 0.076 |
| pep 6 | 0.547 | 0.058 |
| three week culture filterate | 0.986 | 0.073 |

TABLE 4

Cytokine analysis of PBMC's supernatants incubated with the peptides claimed

| | Cytokines (pg/ml) | | | | |
|---|---|---|---|---|---|
| Peptides | gamma-IFN | IL-2 | IL-4 | IL-6 | IL-10 |
| pep 2 | 320 | 280 | 48 | 140 | 80 |
| pep 3 | 168 | 80 | 92 | 620 | 220 |
| pep 4 | 520 | 400 | 28 | 120 | 40 |
| pep 5 | 660 | 260 | 24 | 180 | 36 |
| pep 6 | 240 | 120 | 62 | 760 | 340 |
| three week culture filterate | 380 | 460 | 72 | 540 | 120 |

TABLE 5

Histamine release from sensitised mast cells of ABPA patients by peptides claimed

| Peptides | Histamine released (nM) | |
|---|---|---|
| | Patient | Normal |
| Pep 2 | 402 | 82 |
| pep 3 | 369 | 65 |
| pep 4 | 392 | 58 |
| pep 5 | 356 | 43 |
| pep 6 | 278 | 62 |

Sequence Listing

General Information

1. Sequence characteristics
   (A) Length: 17

(B) Type: Protein (INQQLNPKTNKWEDKRY); (SEQ ID NO: 1)

DNA ATC AAC CAA CAG CTG AAT CCC AAG ACA AAC AAA (SEQ ID NO: 12)
TGG GAA GAC AAG CGG TAC cDNA TAG TTG GTT GTC GAC TTA GGG TTC TGT TTG TTT (SEQ ID NO: 13)
ACC CTT CTG TTC GCC ATG

RNA UAG UUG GUU GUC GAC UUA GGG UUC UGU UUG (SEQ ID NO: 14)
UUU ACC CUU AUG UUC GCC AUG

2. Molecule type: Protein
3. Hypothetical: No
4. Antisense: No
5. Original source
   (A) Organism: *Aspergillus fumigatus*
   (B) Isolate: ATCC strain AF-102; ATCC42202)
   (C) Cell type: Fungus
6. Immediate source
   (A) Library: No
   (B) Clone: No
   (C) Synthetic: Yes
7. Feature
   Name/Key: Pep1, 17 aminoacids peptide
8. Identification method
   (A) How you would identify: Aminoacid sequencing
   (B) Other information: Binds specifically to *A. fumigatus* specific antibodies Information for Sequence ID No. 2

1. Sequence characteristics
   (A) Length: 11

(B) Type: Protein (LNPKTNKWEDK), (SEQ ID NO: 2)

DNA CTG AAT CCC AAG ACA AAC AAA TGG GAA GAC AAG (SEQ ID NO: 15)

cDNA GAC TTA GGG TTC TGT TTG TTT ACC CTT CTG TTC (SEQ ID NO: 16)

RNA GAC UUA GGG UUC UGU UUG UUU ACC CUU AUG UUC (SEQ ID NO: 17)

(C) Standardness: FABMS-1373 amu
2. Molecule type: Protein
3. Hypothetical: No
4. Antisense: No
5. Original source
   (A) Organism: *Aspergillus fumigatus*
   (B) Isolate: ATCC strain AF-102; ATCC-42202)
   (C) Cell type: Fungus
6. Immediate source
   (A) Library: No
   (B) Clone: No
   (C) Synthetic: Yes
7. Feature
   Name/Key: Pep2, 11 aminoacids peptide
8. Identification method
   (A) How you would identify: Aminoacid sequencing
   (B) Other information: Binds specifically to *A. fumigatus* specific antibodies Information for Sequence ID No.3

1. Sequence characteristics
   (A) Length: 8

(B) Type: Protein (INQQLNPK), (SEQ ID NO: 3)

DNA ATC AAC CAA CAG CTG AAT CCC AAG (SEQ ID NO: 18)

cDNA TAG TTG GTT GTC GAC TTA GGG TTC (SEQ ID NO: 19)

RNA UAG UUG GUU GUC GAC UUA GGG UUC (SEQ ID NO: 20)

(C) Standardness: FABMS-954 amu
2. Molecule type: Protein
3. Hypothetical No
4. Antisense: No
5. Original source
   (A) Organism: *Aspergillus fumigatus*
   (B) Isolate: ATCC strain AF-102; ATCC42202)
   (C) Cell type: Fungus
6. Immediate source
   (A) Library: No
   (B) Clone: No
   (C) Synthetic: Yes 7. Feature
   Name/Key: Pep3, 8 aminoacids peptide
8. Identification method
   (A) How you would identify: Aminoacid sequencing
   (B) Other information: Binds specifically to *A. fumigatus* specific antibodies Information for Sequence ID No. 4

1. Sequence characteristics
   (A) Length:15

```
(B) Type: Protein (INQQLNPKTNKWEDK),          (SEQ ID NO: 4)

DNA ATC AAC CAA CAG CTG AAT CCC AAG ACA AAC     (SEQ ID NO: 21)

AAA TGG GAA GAG AAG cDNA TAG TTG GTT GTC GAG TTA GGG TTC TGT TTG    (SEQ ID NO: 22)

TTT ACC CTT CTG TTC

RNA UAG UUG GUU GUC GAC UUA GGG UUC UGU         (SEQ ID NO: 23)

UUG     UUU ACC CUU AUG UUC
```

(C) Standardness: FABMS-1918
2. Molecule type: Protein
3. Hypothetical: No
4. Antisense: No
5. Original source
   (A) Organism: *Aspergillus fumigatus*
   (B) Isolate: ATCC strain AF-102; ATCC42202)
   (C) Cell type: Fungus
6. Immediate source
   (A) Library: No
   (B) Clone: No
   (C) Synthetic: Yes
7. Feature
   Name/Key: Pep 4, 15 aminoacids peptide
8. Identification method
   (A) How you would Identify: Aminoacid sequencing
   (B) Other information: Binds specifically to *A. fumigatus* specific antibodies Information for Sequence ID No.5

1. Sequence characteristics
   (A) Length: 7

```
(B) Type: Protein (TNKWEDK), (SEQ ID NO: 5)

DNA ACA AAC AAA TGG GAA GAC AAG (SEQ ID NO: 24)
```

-continued

```
cDNA TGT TTG TTT ACC CTT CTG TTC (SEQ ID NO: 25)

RNA UGU UUG UUU ACC CUU AUG UUC (SEQ ID NO: 26)
```

(C) Standardness: FABMS-919
2. Molecule type: Protein
3. Hypothetical: No
4. Antisense: No
5. Original source
   (A) Organism: *Aspergillus fumigatus*
   (B) Isolate: ATCC strain AF-102; ATCC42202)
   (C) Cell type: Fungus
6. Immediate source
   (A) Library: No
   (B) Clone: No
   (C) Synthetic: Yes
7. Feature
   Name/Key: Pep5, 7 aminoacids peptide
8. Identification method
   (A) How you would identify: Aminoacid sequencing
   (B) Other information: Binds specifically to *A. fumigatus* specific antibodies Information for Sequence ID No. 6

1. Sequence characteristics
   (A) Length: 13

```
(B) Type: Protein (LNPKTNKWEDKRY),

DNA CTG AAT CCC AAG ACA AAC AAA TGG GAA GAC AAG CCG  (SEQ ID NO: 27)

TAC cDNA GAC TTA GGG TTC TGT TTG TTT ACC CTT CTG TTC GCC (SEQ ID NO: 28)

ATG

RNA GAC UUA GGG UUC UGU UUG UUU ACC CUU AUG UUC      (SEQ ID NO: 29)

GCC AUG
```

(C) Standardness: FABMS-1835
2. Molecule type: Protein
3. Hypothetical: No
4. Antisense: No
5. Original source
   (A) Organism: *Aspergillus fumigatus*
   (B) Isolate: ATCC strain AF-102; ATCC-42202)
   (C) Cell type: Fungus
6. Immediate source
   (A) Library: No
   (B) Clone: No
   (C) Synthetic: Yes 7. Feature
   Name/Key: Pep 6, 13 aminoacids peptide
8. Identification method (A) How you would identify: Aminoacid sequencing
(B) Other Information: Binds specifically to *A. fumigatus* specific antibodies

---

We claim:

1. A method for diagnosing *aspergillosis*, comprising steps of:
   (a) incubating a body fluid sample from a patient with an ELISA plate having at least one peptide bound thereto;
   (b) removing the body fluid sample from the ELISA plate;
   (c) incubating the ELISA plate with anti-human IgG/IgE to form peptide-IgG/IgE complexes;
   (d) removing IgG/IgE not bound in a complex;
   (e) quantitating an amount of peptide-IgG/IgE complexes; and
   (f) diagnosing *aspergillosis* based on the amount of peptide-IgG/IgE complexes,
   wherein the at least one peptide is a peptide comprising an amino acid sequence of one of SEQ ID NOS: 1–6.

2. The method of claim 1, wherein at least one peptide comprises the amino acid sequence of SEQ ID NO: 2.

3. The method of claim 1, wherein the plate is coated with a peptide comprising the amino acid sequence of SEQ ID NO: 2.

4. The method of claim 1, wherein the body fluid sample is blood, cerebrospinal fluid, pleural fluid, or saliva.

5. The method of claim 1, wherein the body fluid sample is blood.

6. The method of claim 1, wherein the IgG/IgE antibody is conjugated to an enzyme and the amount of peptide-IgG/IgE complexes is quantitated by measuring an activity of the enzyme.

7. The method of claim 6, wherein the enzyme is peroxidase or alkaline phosphatase, and wherein an enzyme substrate is o-phenylene diamine or nitroblue tetrazolium.

8. The method of claim 6 wherein at least one peptide consists of an amino acid sequence of one of SEQ ID NOS 1–6.

9. The method of claim 6, wherein at least one peptide consists of the amino acid sequence of SEQ ID NO. 2.

10. A kit for diagnosing *aspergillosis*, comprising an ELISA plate coated with at least one peptide having an amino acid sequence comprising one of SEQ ID NOS: 1–6.

11. The diagnostic kit of claim 10, wherein at least one peptide coating the ELISA plate comprises the amino acid sequence of SEQ ID NO: 2.

12. A method for the diagnosis of *aspergillosis* using at least one peptide comprising an amino acid sequence of SEQ ID NOS: 1–6, said method comprising steps of:
   (a) collecting a body fluid sample containing antibodies specific to *Aspergillus fumigatus* (Af-antibodies) from a patient and separating a fluid containing Af-antibodies from any cells present in the fluid;
   (b) incubating the fluid containing Af-antibodies obtained in step (a) with at least one peptide consisting of an amino acid sequence of SEQ ID NOS: 1–6;
   (c) separating from the resultant incubation mixture residual Af-specific antibodies that do not bind to the at least one peptide in step (b) by centrifugation;
   (d) incubating the residual Af-specific antibodies obtained in step (c) with a mixture of allergens and/or antigens of *Aspergillus fumigatus* coated on a polystyrene ELISA plate to bind antibodies to the ELISA plate;
   (e) washing unbound antibodies from the ELISA plates with an appropriate buffer;
   (f) incubating the washed plates from step (e) with anti-human IgG/IgE conjugated with an enzyme to obtain immobilized enzyme;
   (g) washing unbound enzyme from the ELISA plates with an appropriate buffer;
   (h) adding a soluble substrate for the enzyme; and
   (i) measuring the absorbance values of the wells of ELISA plates in an ELISA reader, wherein the acuteness of *aspergillosis* is inversely related to the absorbance value.

13. The method of claim 12, wherein body fluid may be blood, serum, cerbrospinal fluid, pleural fluids and saliva.

14. The method of claim 12, wherein the buffer used is selected from phosphate buffered saline or Tris buffered saline.

15. The method of claim 12, wherein the conjugate used is selected from anti-human IgG/IgE peroxidase or anti-human IgG/IgE alkaline phosphatase.

16. The method of claim 12, wherein the substrate used is o-phenylene diamine or nitroblue tetrazolium (NBT).

17. A method for diagnosing *aspergillosis* in a patient comprising steps of:
   (a) collecting a blood sample comprising *Aspergillus fumigatus* specific antibodies (Af-antibodies) from a patient and separating a serum from the blood;
   (b) incubating the patient serum containing Af-specific antibodies with a polystyrene ELISA plate having immobilized thereon at least one peptide consisting of the amino acid sequence of SEQ ID NOS: 1–6 to form an immobilized antibody;
   (c) washing the unbound antibodies from the ELISA plate with an appropriate buffer;
   (d) incubating the washed plate from step (c) with anti-human IgG/IgE conjugated with an appropriate enzyme to form an immobilized conjugated enzyme;
   (e) washing the unbound conjugated enzyme from the ELISA plate with an appropriate buffer;
   (f) adding soluble substrate for the enzyme used in step (d) and
   (g) measuring the absorbance values of the wells of the ELISA plate, wherein the acuteness of *aspergillosis* is directly related to the absorbance value.

18. The method of claim 17, wherein the body fluid may be blood, serum, cerbrospinal fluid, pleural fluids and saliva.

19. The method of claim 17, wherein the buffer used is selected from phosphate buffered saline or Tris buffered saline.

20. The method of claim 17, wherein the conjugate used is selected from anti-human IgG/IgE peroxidase or anti-human IgG/IgE alkaline phosphatase.

21. The method of claim 17, wherein the substrate used is o-phenylene diamine or nitroblue tetrazolium (NBT).

* * * * *

SEQUENCE LISTING

<160> NUMBER OF SEQ ID NOS: 29

<210> SEQ ID NO 1
<211> LENGTH: 17
<212> TYPE: PRT
<213> ORGANISM: Aspergillus fumigatus

<400> SEQUENCE: 1

Ile Asn Gln Gln Leu Asn Pro Lys Thr Asn Lys Trp Glu Asp Lys Arg
 1               5                  10                  15

Tyr

<210> SEQ ID NO 2
<211> LENGTH: 11
<212> TYPE: PRT
<213> ORGANISM: Aspergillus fumigatus

<400> SEQUENCE: 2

Leu Asn Pro Lys Thr Asn Lys Trp Glu Asp Lys
 1               5                  10

<210> SEQ ID NO 3
<211> LENGTH: 8
<212> TYPE: PRT
<213> ORGANISM: Aspergillus fumigatus

<400> SEQUENCE: 3

Ile Asn Gln Gln Leu Asn Pro Lys
 1               5

<210> SEQ ID NO 4
<211> LENGTH: 15
<212> TYPE: PRT
<213> ORGANISM: Aspergillus fumigatus

<400> SEQUENCE: 4

Ile Asn Gln Gln Leu Asn Pro Lys Thr Asn Lys Trp Glu Asp Lys
 1               5                  10                  15

<210> SEQ ID NO 5
<211> LENGTH: 7
<212> TYPE: PRT
<213> ORGANISM: Aspergillus fumigatus

<400> SEQUENCE: 5

Thr Asn Lys Trp Glu Asp Lys
 1               5

<210> SEQ ID NO 6
<211> LENGTH: 13
<212> TYPE: PRT
<213> ORGANISM: Aspergillus fumigatus

<400> SEQUENCE: 6

Leu Asn Pro Lys Thr Asn Lys Trp Glu Asp Lys Arg Tyr
 1               5                  10

<210> SEQ ID NO 7

```
<211> LENGTH: 15
<212> TYPE: PRT
<213> ORGANISM: Aspergillus fumigatus

<400> SEQUENCE: 7

Lys Lys Leu Asn Pro Lys Thr Asn Lys Trp Glu Asp Lys Lys Lys
 1               5                  10                  15

<210> SEQ ID NO 8
<211> LENGTH: 20
<212> TYPE: PRT
<213> ORGANISM: Aspergillus fumigatus

<400> SEQUENCE: 8

Ala Thr Pro His Glu Pro Val Phe Phe Ser Trp Asp Ala Gly Ala Val
 1               5                  10                  15

Thr Ser Phe Pro
            20

<210> SEQ ID NO 9
<211> LENGTH: 19
<212> TYPE: PRT
<213> ORGANISM: Aspergillus fumigatus

<400> SEQUENCE: 9

Ala Gln Asn Arg Gln Thr Leu Ala Lys Leu Leu Arg Tyr Gln Ser Thr
 1               5                  10                  15

Lys Ser Gly

<210> SEQ ID NO 10
<211> LENGTH: 18
<212> TYPE: PRT
<213> ORGANISM: Aspergillus fumigatus

<400> SEQUENCE: 10

Ala Thr Trp Thr Cys Ile Asn Gln Gln Leu Asn Pro Lys Thr Asn Lys
 1               5                  10                  15

Trp Glu

<210> SEQ ID NO 11
<211> LENGTH: 19
<212> TYPE: PRT
<213> ORGANISM: Aspergillus fumigatus

<400> SEQUENCE: 11

Ser Ala Arg Asp Glu Ala Gly Leu Asn Glu Ala Val Glu Leu Ala Arg
 1               5                  10                  15

His Ala Lys

<210> SEQ ID NO 12
<211> LENGTH: 51
<212> TYPE: DNA
<213> ORGANISM: Aspergillus fumigatus

<400> SEQUENCE: 12
atcaaccaac agctgaatcc caagacaaac aaatgggaag acaagcggta c         51

<210> SEQ ID NO 13
<211> LENGTH: 51
<212> TYPE: DNA
<213> ORGANISM: Aspergillus fumigatus

<400> SEQUENCE: 13
```
tagttggttg tcgacttagg gttctgtttg tttacccttc tgttcgccat g     51

<210> SEQ ID NO 14
<211> LENGTH: 51
<212> TYPE: RNA
<213> ORGANISM: Aspergillus fumigatus

<400> SEQUENCE: 14
uaguugguug ucgacuuagg guucuguuug uuuacccuua uguucgccau g     51

<210> SEQ ID NO 15
<211> LENGTH: 33
<212> TYPE: DNA
<213> ORGANISM: Aspergillus fumigatus

<400> SEQUENCE: 15
ctgaatccca agacaaacaa atgggaagac aag                          33

<210> SEQ ID NO 16
<211> LENGTH: 33
<212> TYPE: DNA
<213> ORGANISM: Aspergillus fumigatus

<400> SEQUENCE: 16
gacttagggt tctgtttgtt taccttctg ttc                           33

<210> SEQ ID NO 17
<211> LENGTH: 33
<212> TYPE: RNA
<213> ORGANISM: Aspergillus fumigatus

<400> SEQUENCE: 17
gacuuagggu ucuguuuguu uacccuuaug uuc                          33

<210> SEQ ID NO 18
<211> LENGTH: 24
<212> TYPE: DNA
<213> ORGANISM: Aspergillus fumigatus

<400> SEQUENCE: 18
atcaaccaac agctgaatcc caag                                    24

<210> SEQ ID NO 19
<211> LENGTH: 24
<212> TYPE: DNA
<213> ORGANISM: Aspergillus fumigatus

<400> SEQUENCE: 19
tagttggttg tcgacttagg gttc                                    24

<210> SEQ ID NO 20
<211> LENGTH: 24
<212> TYPE: RNA
<213> ORGANISM: Aspergillus fumigatus

<400> SEQUENCE: 20
uaguugguug ucgacuuagg guuc                                    24

<210> SEQ ID NO 21
<211> LENGTH: 45
<212> TYPE: DNA
<213> ORGANISM: Aspergillus fumigatus

<400> SEQUENCE: 21
atcaaccaac agctgaatcc caagacaaac aaatgggaag acaag        45

<210> SEQ ID NO 22
<211> LENGTH: 45
<212> TYPE: DNA
<213> ORGANISM: Aspergillus fumigatus

<400> SEQUENCE: 22
tagttggttg tcgacttagg gttctgtttg tttacccttc tgttc        45

<210> SEQ ID NO 23
<211> LENGTH: 45
<212> TYPE: RNA
<213> ORGANISM: Aspergillus fumigatus

<400> SEQUENCE: 23
uaguugguug ucgacuuagg guucuguuug uuuacccuua uguuc        45

<210> SEQ ID NO 24
<211> LENGTH: 21
<212> TYPE: DNA
<213> ORGANISM: Aspergillus fumigatus

<400> SEQUENCE: 24
acaaacaaat gggaagacaa g        21

<210> SEQ ID NO 25
<211> LENGTH: 21
<212> TYPE: DNA
<213> ORGANISM: Aspergillus fumigatus

<400> SEQUENCE: 25
tgtttgttta cccttctgtt c        21

<210> SEQ ID NO 26
<211> LENGTH: 21
<212> TYPE: RNA
<213> ORGANISM: Aspergillus fumigatus

<400> SEQUENCE: 26
uguuuguuua cccuuauguu c        21

<210> SEQ ID NO 27
<211> LENGTH: 39
<212> TYPE: DNA
<213> ORGANISM: Aspergillus fumigatus

<400> SEQUENCE: 27
ctgaatccca agacaaacaa atgggaagac aagcggtac        39

<210> SEQ ID NO 28
<211> LENGTH: 39
<212> TYPE: DNA
<213> ORGANISM: Aspergillus fumigatus

<400> SEQUENCE: 28
gacttagggt tctgtttgtt tacccttctg ttcgccatg        39

<210> SEQ ID NO 29
<211> LENGTH: 39
<212> TYPE: RNA
<213> ORGANISM: Aspergillus fumigatus -continued

```
<400> SEQUENCE: 29
gacuuagggu ucuguuuguu uacccuuaug uucgccaug                                    39
```